United States Patent [19]
Robinson

[11] Patent Number: 5,639,872
[45] Date of Patent: Jun. 17, 1997

[54] HUMAN VEGF-SPECIFIC OLIGONUCLEOTIDES

[75] Inventor: Gregory S. Robinson, Acton, Mass.

[73] Assignee: Hybridon, Inc., Cambridge, Mass.

[21] Appl. No.: 398,945

[22] Filed: Mar. 2, 1995

Related U.S. Application Data

[63] Continuation-in-part of Ser. No. 378,860, Jan. 26, 1995, which is a continuation-in-part of Ser. No. 98,942, Jul. 27, 1993.

[51] Int. Cl.$^6$ .................... C07H 21/00; A61K 31/70; C12Q 1/68; C12N 5/10
[52] U.S. Cl. .................... 536/24.5; 536/23.5; 536/24.3; 536/24.31; 536/24.33; 435/6
[58] Field of Search .................... 536/24.5, 23.5, 536/24.3, 24.31, 24.33; 514/44; 435/6, 240.2, 33, 34, 36, 8, 9, 11

[56] References Cited

U.S. PATENT DOCUMENTS

| | | | |
|---|---|---|---|
| 5,219,739 | 6/1993 | Tischer et al. | 435/69.4 |
| 5,225,326 | 7/1993 | Bresser et al. | 435/6 |
| 5,271,941 | 12/1993 | Cho-Chung | 424/450 |

FOREIGN PATENT DOCUMENTS

| | | | |
|---|---|---|---|
| WO95/04142 | 2/1995 | WIPO | C12N 15/11 |

OTHER PUBLICATIONS

E. Uhlmann et al. Chem. Rev. 90(4) (Jun. 1990) 543–84.
W. James Antiviral Chemistry & Chemotherapy 2(4) ('91) 191–214.
J. Holz et al. Mol. Cell. Biol. 8(2) (Feb. 1988) 963–73.
D. Tidd Anticancer Res. 10 ('90) 1169–82.
M. Cooney et al. Science 241 (Jul. 22, 1988) 456–9.
J. Milligan et al. J. Med. Chem. 36(14) (Jul. 9, 1993) 1923–37.
C. Stein et al. Science 261 (Aug. 20, 1993) 1004–12.
B. Tseng et al. Cancer Gene Therapy 1(1) (Mar. 1994) 65–71.
P. Westermann et al. Biomed. Bichim. Acta 48(1) ('89) 85–93.
J. Wetmur Cric. Rev. Biochem. Mol. Biol. 26 (3/4) ('91) 227–59.
Pierce et al. (1995) *Investigative Ophthalmology & Visual Science* 36:Abstract 3990.
Smith et al. (1995) *Investigative Ophthalmology & Visual Science* 36:Abstract 3992.
Uchida et al., (1995) *Antisense Res. & Dev.* 5(1):87 (Abstract OP–10).
Nomura et al., (1995) *Antisense Res. & Dev.* 5(1):91 (Abstract OP–18).
Michaelson (1948) *Trans. Ophthalmol. Soc. U. K.* 68:137–180.
Ashton et al. (1954) *Br. J. Ophthalmol.* 38:397–432.
*Am. J. Ophthalmol.* (1976) 81:383–396.
Senger et al. (1986) *Cancer Res.* 46:5629–5632.
Folkman et al. (1987) *Science* 235:442–446.
*Ophthalmol.* (1991) 98:741–840 (Supplement).
Klagsbrun et al. (1991) *Ann. Rev. Physiol.* 53:217–239.
Tischer et al. (1991) *J. Biol. Chem.* 266:11947–11954.
Claffey et al. (1992) *J. Biol. Chem.* 267:16317–16322.
Plate et al. (1992) *Nature* 359:845–848.
Plouet et al. (1992) *Invest. Ophthalmol. Vis. Sci.* 34:900.
Schweiki et al. (1992) *Nature* 359:843–845.
Adamis et al. (1993) *Biochem. Biophys. Res. Commun.* 193:631–638.
Adamis et al. (1993) *Invest. Ophthalmol. Vis. Sci.* 34:1440.
Kim et al. (1993) *Nature* 362:841–844.
Knighton et al. (1983) *Science* 221:1283–1285.
Miller et al. (1993) *Principles and Practice of Ophthalmology*, W.B. Saunders, Philadelphia, pp. 760.
Aiello et al. (1994) *New Eng. J. Med.* 331:1480–1487.
Aiello et al. (1994) *Invest. Ophthalmol. Vis. Sci.* 35:1868.
Bressler et al., *Principles and Practices of Ophthalmology* (eds. Albert and Jakobiac), W.B. Saunders Co., Philadelphia, PA) (1994) vol. 2.
Foster in *Harrison's Principles of Internal Medicine* (Isselbacher et al., eds.) McGraw–Hill, Inc., New York (1994) pp. 1994–1995.
Pierce et al. (1994) *Int. Ophth. Clinics* 34:121–148.
Simorre–Pinatel et al. (1994) *Invest. Ophthalmol. Vis. Sci.* 35:3393–3400.
Smith et al. (1994) *Invest. Ophthalmol. Vis. Sci.* 35:1442.
Smith et al. (1994) *Invest. Ophthalmol. Vis. Sci.* 35:101–111.
Focus (Jan. 6, 1995).
*Ophthalmology World News* (1995) p. 26.
*Ophthalmology Times* (Jan. 16–22, 1995).
Pierce et al. (1995) *Proc. Natl. Acad. Sci. (USA)* 92 (Jan. '95) 905–9.
Monacci et al. (1993) *American Journal Of Physiology* 264:c995–c1002.
Garrido et al. (1993) *Growth Factors* 8:109–117.

*Primary Examiner*—Charles C. P. Rories
*Attorney, Agent, or Firm*—Hale and Dorr LLP

[57] ABSTRACT

Disclosed are methods of reducing neovascularization and of treating various disorders associated with neovascularization. These methods include administering to a tissue or subject a synthetic oligonucleotide specific for vascular endothelial growth factor nucleic acid effective in inhibiting the expression of vascular endothelial growth factor.

1 Claim, 4 Drawing Sheets

HUMAN VEGF-SPECIFIC OLIGONUCLEOTIDES

CROSS-REFERENCE TO RELATED APPLICATIONS

This application is a continuation-in-part of copending patent application Ser. No. 08/378,860 entitled "Inhibition of Neovascularization Using VEGF-Specific Oligonucleotides", filed 26 Jan., 1995, which is a continuation-in-part of copending patent application Ser. No. 08/098,942 entitled "Antisense Oligonucleotide Inhibition of Vascular Endothelial Growth Factor Expression, filed 27 Jul., 1993.

FUNDING

This invention was made with Government support under Grant No. RO1 EYO869 awarded by the National Institutes of Health. Thus, the Government has certain rights in the invention.

BACKGROUND OF THE INVENTION

This invention relates to neovascularization. More specifically, this invention relates to treatment of disorders that are associated with neovascularization using oligonucleotides specific for vascular endothelial growth factor.

Neovascular diseases of the retina such as diabetic retinopathy, retinopathy of prematurity, and age-related macular degeneration are a major cause of blindness in the United States and the world, yet the biochemical events responsible for these processes have not been fully elucidated.

Diabetic retinopathy is the leading cause of blindness among working age adults (20–64) in the United States (Foster in *Harrion's Principles of Internal Medicine* (Isselbacher et al., eds.) McGraw-Hill, Inc., New York (1994) pp. 1994–1995). During the course of diabetes mellitus, the retinal vessels undergo changes that result in not only leaky vessels but also vessel drop out resulting in retinal hypoxia. The effects of these complications are hemorrhaging, "cotton wool" spots, retinal infarcts, and neovascularization of the retina resulting in bleeding and retinal detachment. If left untreated, there is a 60% chance of visual loss. Classic treatment for proliferative diabetic retinopathy is panretinal laser photocoagulation (PRP). However, complications can occur from panretinal laser photocoagulation such as foveal burns, hemorrhaging, retinal detachment, and choroidal vessel growth. Furthermore, other untoward effects of this treatment are decreased peripheral vision, decreased night vision, and changes in color perception (*Am. J. Ophthalmol.* (1976) 81:383–396; *Ophthalmol.* (1991) 98:741–840).

Thus, there is a need for a more effective treatment for diabetic retinopathy.

Retinopathy of prematurity (ROP) is a common cause of blindness in children in the United States (Pierce et al. (1994) *Int. ophth. Clinics* 34:121–148). Premature babies are exposed to hyperoxic conditions after birth even without supplemental oxygen because the partial pressure of oxygen in utero is much lower than what is achieved when breathing normal room air. This relative hyperoxia is necessary for their survival yet can result in ROP. The blood vessels of the retina cease to develop into the peripheral retina resulting in ischemia and localized hypoxic conditions as the metabolic demands of the developing retina increase. The resulting hypoxia stimulates the subsequent neovascularization of the retina. This neovascularization usually regresses but can lead to irreversible vision loss. There are at least 10,000 new cases per year with a worldwide estimate of 10 million total cases. At present, there is no effective cure for ROP. Two therapeutic methods, cryotherapy and laser therapy, have been used but are not completely effective and themselves cause damage to the eye, resulting in a reduction of vision (Pierce et al. (1994) *Int. Ophth. Clinics* 34:121–148). Many other antiangiogenic compounds have been tested, but no inhibition in retinal neovascularization has been reported (Smith et al. (1994) *Invest. Ophthalmol. Vis. Sci.* 35:1442; Foley et al. (1994) *Invest. Ophthalmol. Vis. Sci.* 35:1442).

Thus, there is a need for an effective treatment for ROP.

Age related macular degeneration is one of the leading causes of blindness in older adults in the United States, and may account for up to 30% of all bilateral blindness among Caucasian Americans (Anonymous (1994) *Prevent Blindness America*). This disease is characterized by loss of central vision, usually in both eyes, due to damage to retinal pigment epithelial cells which provide physiological support to the light sensitive photoreceptor cells of the retina. In most cases there is currently no effective treatment. In approximately 20% of exudative cases that are diagnosed early, laser treatment can prevent further loss of vision; however, this effect is temporary (Bressler et al., *Principles and Practices of Ophthalmology* (eds. Albert and Jakobiac), W. B. Saunders Co., Philadelphia, Pa.) (1994) Vol. 2 pp. 834–852).

Thus, there is a need for a more effective and permanent treatment for age related macular degeneration.

Ocular neovascularization is also the underlying pathology in sickle cell retinopathy, neovascular glaucoma, retinal vein occlusion, and other hypoxic diseases. These eye diseases as well as other pathological states associated with neovascularization (i.e., tumor growth, wound healing) appear to have hypoxia as a common factor (Knighton et al. (1983) *Science* 221:1283–1285; Folkman et al. (1987) *Science* 235:442–446; Klagsbrun et al. (1991) *Ann. Rev. Physiol.* 53:217–239; Miller et al. (1993) *Principles and Practice of Ophthalmology*, W. B. Saunders, Philadelphia, pp. 760; and Aiello et al. (1994) *New Eng. Med.* 331:1480–1487). Moreover, retinal neovascularization has been hypothesized to be the result of a "vasoformative factor" which is released by the retina in response to hypoxia (Michaelson (1948) *Trans. Ophthalmol. Soc. U. K.* 68:137–180; and Ashton et al. (1954) *Br. J. Ophthalmol* 38:397–432). Recent experimental data show a high correlation between vascular endothelial growth factor expression and retinal neovascularization (Aiello et al. (1994) *New Eng. J. Med.* 331:1480–1487). Furthermore, elevated levels of vascular endothelial growth factor have recently been found in vitreous from patients with diabetes (Aiello et al., ibid.). Thus, this cytokine/growth factor may play an important role in neovascularization- related disease.

Vascular endothelial growth factor/vascular permeability factor (VEGF/VPF) is an endothelial cell-specific mitogen which has recently been shown to be stimulated by hypoxia and required for tumor angiogenesis (Senger et al. (1986) *Cancer* 46:5629–5632; Kim et al. (1993) *Nature* 362:841–844; Schweiki et al. (1992) *Nature* 359:843–845; Plate et al. (1992) *Nature* 359:845–848). It is a 34–43 kDa (with the predominant species at about 45 kDa) dimeric, disulfide-linked glycoprotein synthesized and secreted by a variety of tumor and normal cells. In addition, cultured human retinal cells such as pigment epithelial cells and pericytes have been demonstrated to secrete VEGF and to increase VEGF gene expression in response to hypoxia (Adamis et al. (1993) *Biochem. Biophys. Res. Commun.* 193:631–638; plouet et al. (1992) *Invest. Ophthalmol. Vis. Sci.* 34:900; Adamis et al. (1993) *Invest. Ophthalmol. Vis. Sci.* 34:1440; Aiello et al. (1994) *Invest. Ophthalmol. Vis. Sci.* 35: 1868; simorre-Pinatel et al. (1994) *Invest. Ophthalmol. Vis. Sci.* 35:3393–3400). In contrast, VEGF in normal tissues is relatively low. Thus, VEGF appears to play a principle role in many pathological states and processes related to neovascularization. Regulation of VEGF expression in tissues affected by the various conditions described above could therefore be key in treatment or preventative therapies associated with hypoxia.

SUMMARY OF THE INVENTION

It is known that cells affected by hypoxia induce VEGF. It has now been discovered that synthetic oligonucleotides specific for the mRNA for VEGF can inhibit hypoxia-associated neovascularization. This information has been exploited to develop the present invention which includes methods of reducing neovascularization and of treating disorders and diseases related to neovascularization. As used herein, the term "neovascularization" refers to the growth of blood vessels and capillaries.

In the methods of the invention, an amount of a synthetic oligonucleotide specific for vascular endothelial growth factor nucleic acid and effective in inhibiting the expression of vascular endothelial growth factor is administered to a neovascularized tissue. This tissue may be a culture or may be part or the whole body of an animal such as a human or other mammal.

As used herein, the term "synthetic oligonucleotide" refers to chemically synthesized polymers of nucleotides covalently attached via at least one 5' to 3' internucleotide linkage. In some embodiments, these oligonucleotides contain at least one deoxyribonucleotide, ribonucleotide, or both deoxyribonucleotides and ribonucleotides. In another embodiment, the synthetic oligonucleotides used in the methods of the invention are from about 14 to about 28 nucleotides in length. In preferred embodiments, these oligonucleotides contain from about 15 to about 25 nucleotides.

In some embodiments, the oligonucleotides may also be modified in a number of ways without compromising their ability to hybridize to nucleotide sequences contained within the mRNA for VEGF. The term "modified oligonucleotide" as used herein describes an oligonucleotide in which at least two of its nucleotides are covalently linked via a synthetic linkage, i.e., a linkage other than a phosphodiester linkage between the 5' end of one nucleotide and the 3' end of another nucleotide in which the 5' nucleotide phosphate has been replaced with any number of chemical groups.

In some embodiments, at least one internucleotide linkage of the oligonucleotide is an alkylphosphonate, phosphorothioate, phosphorodithioate, phosphate ester, alkylphosphonothioate, phosphoramidate, carbamate, carbonate, phosphate triester, acetamidate, and/or carboxymethyl ester.

The term "modified oligonucleotide" also encompasses oligonucleotides with a modified base and/or sugar. In addition, unoxidized or partially oxidized oligonucleotides having a substitution in one nonbridging oxygen per nucleotide in the molecule are considered to be modified oligonucleotides. Also considered as modified oligonucleotides are oligonucleotides having nuclease resistance-conferring bulky substituents at their 3' and/or 5' end(s) and/or various other structural modifications not found in vivo without human intervention. Other modifications include those which are internal or are at the end(s) of the oligonucleotide molecule and include additions to the molecule of the internucleoside phosphate linkages, and terminal ribose, deoxyribose and phosphate modifications which cleave, or crosslink to the opposite chains or to associated enzymes or other proteins which bind to the genome or RNA.

A method of treating retinopathy of prematurity (ROP) is provided. This method comprises the step of administering to a subject afflicted with ROP a therapeutic amount of an oligonucleotide specific for vascular endothelial growth factor nucleic acid and effective in inhibiting the expression of vascular endothelial growth factor in the retina.

In another aspect of the invention, a method of treating diabetic retinopathy is provided. This method includes administering to a subject afflicted with diabetic retinopathy a therapeutic amount of an oligonucleotide specific for vascular endothelial growth factor nucleic acid and effective in inhibiting the expression of VEGF in the retina.

In yet another aspect of the invention, a method of treating age-related macular degeneration (ARMD) is provided, which includes comprising the step of administering to a subject afflicted with ARMD a therapeutic amount of an oligonucleotide specific for vascular endothelial growth factor nucleic acid effective in inhibiting the expression of VEGF in the retina.

In some preferred embodiments of the methods of the invention described above, the oligonucleotide is administered locally (e.g., intraocularly or interlesionally) and/or systemically. The term "local administration" refers to delivery to a defined area or region of the body, while the term "systemic administration" is meant to encompass delivery to the whole organism by oral ingestion, or by intramuscular, intravenous, subcutaneous, or intraperitoneal injection.

Another aspect of the invention includes pharmaceutical compositions capable of inhibiting neovascularization and thus are useful in the methods of the invention. These compositions include a synthetic oligonucleotide which specifically inhibits the expression of vascular endothelial growth factor and a physiologically and/or pharmaceutically acceptable carrier.

The term "pharmaceutically acceptable" means a non-toxic material that does not interfere with the effectiveness of the biological activity of the active ingredient(s). The term "physiologically acceptable" refers to a non-toxic material that is compatible with a biological system such as a cell, cell culture, tissue, or organism.

Another aspect of the invention is assessment of the role of VEGF in neovascularization associated with disease states.

BRIEF DESCRIPTION OF THE DRAWINGS

The foregoing and other objects of the present invention, the various features thereof, as well as the invention itself may be more fully understood from the following description, when read together with the accompanying drawings in which.

DETAILED DESCRIPTION OF THE PREFERRED EMBODIMENTS

Figure 1:
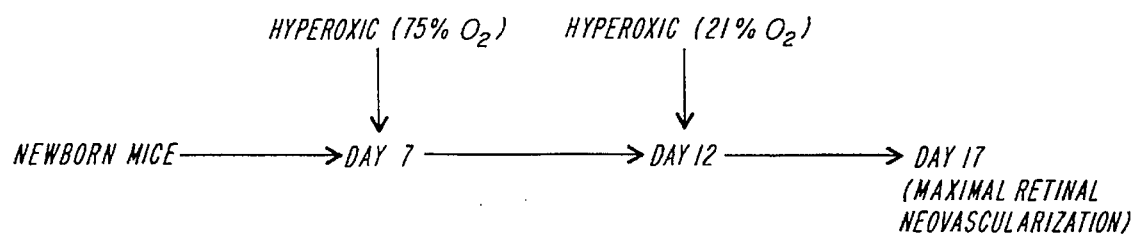
FIG. 1 is a diagrammatic representation of the murine model for retinal neovascularization.

The patent and scientific literature referred to herein establishes the knowledge that is available to those with skill in the art. The issued U.S. patents, allowed applications, and references cited herein are hereby incorporated by reference.

The present invention provides synthetic antisense oligonucleotides specific for VEGF nucleic acid which are useful in treating diseases and disorders associated with neovascularization including retinal neovascularization.

Antisense oligonucleotide technology provides a novel approach to the inhibition of gene expression (see generally, Agrawal (1992) *Trends in Biotech.* 10:152; Wagner (1994) *Nature* 372:333–335; and Stein et al. (1993) *Science* 261:1004–1012). By binding to the complementary nucleic acid sequence (the sense strand), antisense oligonucleotide are able to inhibit splicing and translation of RNA. In this way, antisense oligonucleotides are able to inhibit protein expression. Antisense oligonucleotides have also been shown to bind to genomic DNA, forming a triplex, and inhibit transcription. Furthermore, a 17 mer base sequence statistically occurs only once in the human genome, and thus extremely precise targeting of specific sequences is possible with such antisense oligonucleotides.

It has been determined that the VEGF coding region is comprised of eight axons (Tischer et al. (1994) *J. Biol. Chem.* 266:11947–11954). Three VEGF transcripts, 121, 165, and 189 amino acids long, have been observed, suggesting that an alternative splicing mechanism is involved (Leung et al. (1989) *Science* 246:1306–1309; Tischer et al. (1991) *J. Biol. Chem.* 266:11947–11954). More recently, a fourth VEGF transcript was discovered which has a length encoding 206 amino acids (Houck et al. (1991) *Mol. Endocrinol.* 5:1806–1814). Transcripts analogous to the 121 and 165 amino acid polypeptides have been identified in the bovine system (Leung et al. (1989) *Science* 246:1306–1309), and the transcript corresponding to the 165 amino acid transcript have also been identified in the rodent system (Conn et al. (1990) *Proc. Natl. Acad. Sci.* (USA) 87:1323–1327); Senger et al. (1990) *Cancer Res.* 50:1774–1778; Claffey et al. (1992) *J. Biol. Chem.* 267:16317–16322). Nucleic acid sequences encoding three forms of VEGF have also been reported in humans (Tischer et al. (1991) *J. Biol. Chem.* 266:11947–11954), and comparisons between the human and the murine VEGF have revealed greater than 85% interspecies conservation (Claffey et al. (1992) *J. Biol. Chem.* 267:16317–16322).

The oligonucleotides of the invention are directed to any portion of the VEGF nucleic acid sequence that effectively acts as a target for inhibiting VEGF expression. The sequence of the gene encoding VEGF has been reported in mice (Claffey et al., ibid.) and for humans (Tischer et al., ibid.). These targeted regions of the VEGF gene include any portions of the known exons. In addition, exon-intron boundaries are potentially useful targets for antisense inhibition of VEGF expression.

The nucleotide sequences of some representative, non-limiting oligonucleotides specific for human VEGF are listed below in TABLE 1.

TABLE 1

| OLIGO | TARGETED SITE | SEQUENCE (AS) | SEQ ID NO: |
|---|---|---|---|
| H-1 | 21-2 | 5'-CGCCGGGCCGCCAGCACACT-3' | 1 |
| H-1R | 21-2 | 5'-CGCCGGGCCGCCAGCACACU-3' | 2 |
| H-1A | 16-2 | 5'-GGCCGCCAGCACACT-3' | 3 |
| H-1B | 26-2 | 5'-GCTCGCGCCGGGCCGCCAGCACACT-3' | 4 |
| H-2 | 76-57 | 5'-CAAGACAGCAGAAAGTTCAT-3' | 5 |
| H-3 | 80-62 | 5'-CACCCAAGACAGCAGAAAG-3' | 6 |
| H-3A | 80-66 | 5'-CACCCAAGACAGCAG-3' | 7 |
| H-3B | 86-62 | 5'-CCAATGCACCCAAGACAGCAGAAAG-3' | 8 |
| H-4 | 64-45 | 5'-AAGTTCATGGTTTCGGAGGC-3' | 10 |
| H-5 | 62-43 | 5'-GTTCATGGTTTCGGAGGCCC-3' | 11 |
| H-6 | 138-119 | 5'-GTGCAGCCTGGGACCACTTG-3' | 12 |
| H-7 | 628-609 | 5'-CGCCTCGGCTTGTCACATCT-3' | 13 |
| H-8 | 648-629 | 5'-CTTCCTCCTGCCCGGCTCAC-3' | 14 |
| H-8R | 648-629 | 5'-CUUCCUCCUGCCCGGCUCAC-3' | 15 |
| H-8A | 648-634 | 5'-CTTCCTCCTGCCCGG-3' | 16 |
| H-8B | 653-629 | 5'-GGCTCCTTCCTCCTGCCCGGCTCAC-3' | 17 |
| H-9 | 798-779 | 5'-GTCTCCTCTTCCTTCATTTC-3' | 18 |
| H-9A | 798-784 | 5'-GTCTCCTCTTCCTTC-3' | 19 |
| H-9B | 803-779 | 5'-GCAGAGTCTCCTCTTCCTTCATTTC-3' | 20 |
| H-10 | 822-803 | 5'-CGGACCCAAAGTGCTCTGCG-3' | 21 |
| H-10A | 817-803 | 5'-CCAAAGTGCTCTGCG-3' | 22 |
| H-10B | 827-803 | 5'-CCCTCCGGACCCAAAGTGCTCTGCG-3' | 23 |
| H-11 | E1-I1 | 5'-GGGCACGACCGCTTACCTTG-3' | 24 |
| H-12 | I1-E2 | 5'-GGGACCACTGAGGACAGAAA-3' | 25 |
| H-13 | I2-E3 | 5'-CACCACTGCATGAGAGGCGA-3' | 26 |
| H-14 | E3-I3 | 5'-TCCCAAAGATGCCCACCTGC-3' | 27 |
| H-15 | I3-E4 | 5'-CGCATAATCTGGAAAGGAG-3' | 28 |
| H-17 | 59-40 | 5'-CATGGTTTCGGAGGCCCGAC-3' | 30 |
| H-17B | 59-40 | 5'-CAUGGUUCGGAGGCCCGAC-3' | 31 |
| H-18 | 61-42 | 5'-TTCATGGTTTCGGAGGCCCG-3' | 32 |

TABLE 1-continued

| OLIGO | TARGETED SITE | SEQUENCE (AS) | SEQ ID NO: |
|---|---|---|---|
| E1/I1 | E1/I1 | 5'-GACCGCTTACCTTGGCATGG-3' | 33 |
| I1/E2 | I1/E2 | 5'-CCTGGGACCACTGAGGACAG-3' | 34 |
| E2/I2 | E2/I2 | 5'-GGGACTCACCTTCGTGATGA-3' | 35 |
| I2/E3 | I2/E3 | 5'-GAACTTCACCACTGCATGAG-3' | 36 |
| E3/I3 | E3/I3 | 5'-TCCCAAAGATGCCCACCTGC-3' | 37 |
| I3/E4 | I3/E4 | 5'-GCATAATCTGGAAAGGAAGG-3' | 38 |
| E4/I4 | E4/I4 | 5'-ACATCCTCACCTGCATTCAC-3' | 39 |
| E4/I4B | E4/I4 | 5'-ACATCCUCACCTGCAUUCAC-3' | 40 |
| I4/E5 | I4/E5 | 5'-TTTCTTTGGTCTGCAATGGG-3' | 41 |
| E5/I5 | E5/I5 | 5'-GGCCACTTACTTTTCTTGTC-3' | 42 |
| I5/E7 | I5/E7 | 5'-CACAGGGACTGGAAAATAAA-3' | 43 |
| E7/I7 | E7/I7 | 5'-GGGAACCAACCTGCAAGTAC-3' | 44 |
| I7/E8 | I7/E8 | 5'-GTCACATCTGAGGGAAATGG-3' | 45 |
| VH | 641-621 | 5'-CTGCCCGGCTCACCGCCTCGG-3 | 46 |
| H-19 | 56-38 | 5'-GGTTTCGGAGGCCCGACCG-3' | 50 |

With the published nucleic acid sequences and this disclosure provided, those of skill in the art will be able to identify, with without undue experimentation, other antisense nucleic acid sequences that inhibit VEGF expression. For example, other sequences targeted specifically to human VEGF nucleic acid can be selected based on their ability to be cleaved by RNAse H.

The oligonucleotides of the invention are composed of ribonucleotides, deoxyribonucleotides, or a combination of both, with the 5' end of one nucleotide and the 3' end of another nucleotide being covalently linked. These oligonucleotides are at least 14 nucleotides in length, but are preferably 15 to 28 nucleotides long, with 15 to 25 mers being the most common.

These oligonucleotides can be prepared by the art recognized methods such as phosphoramidate or H-phosphonate chemistry which can be carried out manually or by an automated synthesizer as described in Uhlmann et al. (*Chem. Rev.* (1990) 90:534–583).

The oligonucleotides of the invention may also be modified in a number of ways without compromising their ability to hybridize to VEGF mRNA. For example, the oligonucleotides may contain other than phosphodiester internucleotide linkages between the 5' end of one nucleotide and the 3' end of another nucleotide in which the 5' nucleotide phosphodiester linkage has been replaced with any number of chemical groups. Examples of such chemical groups include alkylphosphonates, phosphorothioates, phosphorodithioates, alkylphosphonothioates, phosphoramidates, phosphate esters, carbamates, acetamidate, carboxymethyl esters, carbonates, and phosphate triesters. Oligonucleotides with these linkages can be prepared according to known methods (see, e.g., Uhlmann et al. (1990) *Chem. Rev.* 90:543–583).

Other modifications include those which are internal or at the end(s) of the oligonucleotide molecule and include additions to the molecule of the internucleoside phosphate linkages, such as cholesteryl or diamine compounds with varying numbers of carbon residues between the amino groups and terminal ribose, deoxyribose and phosphate modifications which cleave, or crosslink to the opposite chains or to associated enzymes or other proteins which bind to the genome. Examples of such modified oligonucleotides include oligonucleotides with a modified base and/or sugar such as 2'-O-alkylated ribose, arabinose instead of ribose, or a 3', 5'-substituted oligonucleotide having a sugar which, at both its 3' and 5' positions is attached to a chemical group other than a hydroxyl group (at its 3' position) and other than a phosphate group (at its 5' position). Other modified oligonucleotides are capped with a nuclease resistance-conferring bulky substituent at their 3' and/or 5' end(s), or have a substitution in one nonbridging oxygen per nucleotide. Such modifications can be at some or all of the internucleoside linkages, as well as at either or both ends of the oligonucleotide and/or in the interior of the molecule.

The preparation of these modified oligonucleotides is well known in the art (reviewed in Agrawal et al. (1992) *Trends Biotechnol.* 10:152–158). For example, nucleotides can be covalently linked using art-recognized techniques such as phosphoramidate, H-phosphonate chemistry, or methylphosphoramidate chemistry (see, e.g., Uhlmann et al. (1990) *Chem. Rev.* 90:543–584; Agrawal et al. (1987) *Tetrahedron. Lett.* 28: (31) :3539–3542); Caruthers et al. (1987) *Meth. Enzymol.* 154:287–313; U.S. Pat. No. 5,149,798). Oligomeric phosphorothioate analogs can be prepared using methods well known in the field such as methoxyphosphoramidite (see, e.g., Agrawal et al. (1988) *Proc. Natl. Acad. Sci. (USA)* 85:7079–7083) or H-phosphonate (see, e.g., Froehler (1986) *Tetrahedron Lett.* 27: 5575–5578) chemistry. The synthetic methods described in Bergot et al. (*J. Chromatog.* (1992) 559:35–42) can also be used.

The synthetic antisense oligonucleotides of the invention in the form of a therapeutic formulation are useful in treating diseases, and disorders, and conditions associated with neovascularization including, but not limited to, retinal neovascularization, tumor growth, and wound healing.

The synthetic oligonucleotides of the invention may be used as part of a pharmaceutical composition when combined with a physiologically and/or pharmaceutically acceptable carrier. The characteristics of the carrier will depend on the route of administration. Such a composition may contain, in addition to the synthetic oligonucleotide and carrier, diluents, fillers, salts, buffers, stabilizers, solubilizers, and other materials well known in the art. The pharmaceutical composition of the invention may also contain other active factors and/or agents which enhance inhibition of VEGF expression or which will reduce neovascularization. For example, combinations of synthetic oligonucleotides, each of which is directed to different regions of the VEGF mRNA, may be used in the pharmaceutical compositions of the invention. The pharmaceutical composition of the invention may further contain nucleotide analogs such as azidothymidine, dideoxycytidine, dideosyinosine, and the like. Such additional factors and/or agents may be included in the pharmaceutical composition to produce a synergistic effect with the synthetic oligonucleotide of the invention, or to minimize side-effects caused by the synthetic oligonucleotide of the invention. Conversely, the synthetic oligonucleotide of the invention may be included in formulations of a particular anti-VEGF or anti-neovascularization factor and/or agent to minimize side effects of the anti-VEGF factor and/or agent.

The pharmaceutical composition of the invention may be in the form of a liposome in which the synthetic oligonucleotides of the invention is combined, in addition to other pharmaceutically acceptable carriers, with amphipathic agents such as lipids which exist in aggregated form as micelles, insoluble monolayers, liquid crystals, or lamellar layers which are in aqueous solution. Suitable lipids for liposomal formulation include, without limitation, monoglycerides, diglycerides, sulfatides, lysolecithin, phospholipids, saponin, bile acids, and the like. One particularly useful lipid carrier is lipofectin. Preparation of such liposomal formulations is within the level of skill in the art, as disclosed, for example, in U.S. Pat. No. 4,235,871; U.S. Pat. No. 4,501,728; U.S. Pat. No. 4,837,028; and U.S. Pat. No. 4,737,323. The pharmaceutical composition of the invention may further include compounds such as cyclodextrins and the like which enhance delivery of oligonucleotides into cells, as described by Zhao et al. (in press), or slow release polymers.

As used herein, the term "therapeutically effective amount" means the total amount of each active component of the pharmaceutical composition or method that is sufficient to show a meaningful patient benefit, i.e., healing of chronic conditions characterized by neovascularization or a reduction in neovascularization, itself, or in an increase in rate of healing of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of treatment or use of the present invention, a therapeutically effective amount of one or more of the synthetic oligonucleotide of the invention is administered to a subject afflicted with a disease or disorder related to neovascularization, or to a tissue which has been neovascularized. The synthetic oligonucleotide of the invention may be administered in accordance with the method of the invention either alone of in combination with other known therapies for neovascularization. When co-administered with one or more other therapies, the synthetic oligonucleotide of the invention may be administered either simultaneously with the other treatment(s), or sequentially. If administered sequentially, the attending physician will decide on the appropriate sequence of administering the synthetic oligonucleotide of the invention in combination with the other therapy.

Administration of the synthetic oligonucleotide of the invention used in the pharmaceutical composition or to practice the method of the present invention can be carried out in a variety of conventional ways, such as intraocular, oral ingestion, inhalation, or cutaneous, subcutaneous, intramuscular, or intravenous injection.

When a therapeutically effective amount of synthetic oligonucleotide of the invention is administered orally, the synthetic oligonucleotide will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% synthetic oligonucleotide and preferably from about 25 to 90% synthetic oligonucleotide. When administered in liquid form, a liquid carrier such as water, petroleum, oils of animal or plant origin such as peanut oil, mineral oil, soybean oil, sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of the synthetic oligonucleotide and preferably from about 1 to 50% synthetic oligonucleotide.

When a therapeutically effective amount of synthetic oligonucleotide of the invention is administered by intravenous, subcutaneous, intramuscular, intraocular, or intraperitoneal injection, the synthetic oligonucleotide will be in the form of a pyrogen-free, parenterally acceptable aqueous solution. The preparation of such parenterally acceptable solutions, having due regard to pH, isotonicity, stability, and the like, is within the skill in the art. A preferred pharmaceutical composition for intravenous, subcutaneous, intramuscular, intraperitoneal, or intraocular injection should contain, in addition to the synthetic oligonucleotide, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art.

The amount of synthetic oligonucleotide in the pharmaceutical composition of the present invention will depend upon the nature and severity of the condition being treated, and on the nature of prior treatments which the patent has undergone. Ultimately, the attending physician will decide the amount of synthetic oligonucleotide with which to treat each individual patient. Initially, the attending physician will administer low doses of the synthetic oligonucleotide and observe the patient's response. Larger doses of synthetic oligonucleotide may be administered until the optimal therapeutic effect is obtained for the patient, and at that point the dosage is not increased further. It is contemplated that the various pharmaceutical compositions used to practice the method of the present invention should contain about 10 µg to about 20 mg of synthetic oligonucleotide per kg body or organ weight.

The duration of intravenous therapy using the pharmaceutical composition of the present invention will vary, depending on the severity of the disease being treated and the condition and potential idiosyncratic response of each individual patient. Ultimately the attending physician will decide on the appropriate duration of intravenous therapy using the pharmaceutical composition of the present invention.

Some diseases lend themselves to acute treatment while others require to longer term therapy. Proliferative retinopathy can reach a threshold in a matter of days as seen in ROP, some cases of diabetic retinopathy, and neovascular glaucoma. Premature infants are at risk for neovascularization around what would be 35 weeks gestation, a few weeks after birth, and will remain at risk for a short period of time until the retina becomes vascularized. Diabetic retinopathy can be acute but may also smolder in the proliferative phase for considerably longer. Diabetic retinopathy will eventually become quiescent as the vasoproliferative signal diminishes with neovascularization or destruction of the retina.

Both acute and long term intervention in retinal disease are worthy goals. Intravitreal injections of oligonucleotides against VEGF can be an effective means of inhibiting retinal neovascularization in an acute situation. However for long term therapy over a period of years, systemic delivery (intraperitoneal, intramuscular, subcutaneous, intravenous) either with carriers such as saline, slow release polymers, or liposomes should be considered.

In some cases of chronic neovascular disease, systemic administration of oligonucleotides may be preferable. Since the disease process concerns vessels which are abnormal and leaky, the problem of passage through the blood brain barrier may not be a problem. Therefore, systemic delivery may prove efficacious. The frequency of injections is from continuous infusion to once a month, depending on the disease process and the biological half life of the oligonucleotides.

In addition to inhibiting neovascularization in vivo, antisense oligonucleotides specific for VEGF are useful in determining the role of this cytokine in processes where neovascularization is involved. For example, this technology is useful in in vitro systems which mimic blood vessel formation and permeability, and in vivo system models of neovascularization, such as the murine model described below.

A murine model of oxygen-induced retinal neovascularization has been established which occurs in 100% of treated animals and is quantifiable (Smith et al. (1994) *Invest. Ophthalmol. Vis. Sci.* 35:101–111). Using this model, a correlation has been determined between increasing expression of VEGF message and the onset of retinal neovascularization in the inner nuclear and ganglion cell layers (i.e., in Müller cells) (Pierce et al. (1995) *Proc. Natl. Acad. Sci.* (USA) (in press). This result has been confirmed by Northern blot and in situ hybridization analysis of whole retinas at different time points during the development of neovascularization (Pierce et al., ibid.).

That VEGF plays a role in retinal neovascularization has been shown using the murine model of neovascularization described above. Three independent experiments were performed using antisense oligonucleotides specific for VEGF (JG-3 (SEQ ID NO:47), JG-4, (SEQ ID NO:48), and Vm (SEQ ID NO:46), and a corresponding sense oligonucleotide (V2 (SEQ ID NO:49). These oligonucleotides were designed using the known nucleic sequence of murine VEGF (Claffee et al. (1992) *J. Biol. Chem.* 267:16317–16322). The sequence of the Vm oligonucleotide (SEQ ID NO:46) is targeted to the sequence surrounding the translational TGA stop site (TGA). The sequence of JG-4 (SEQ ID NO:48) is targeted to the sequence 5' to and containing the ATG of the translational start site of the murine VEGF molecule. The sequence of JG-3 (SEQ ID NO:47) is targeted to the 5' untranslated region, and the V2 sense sequence is targeted to the sequence surrounding the translational start site (ATG).

Figure 2:
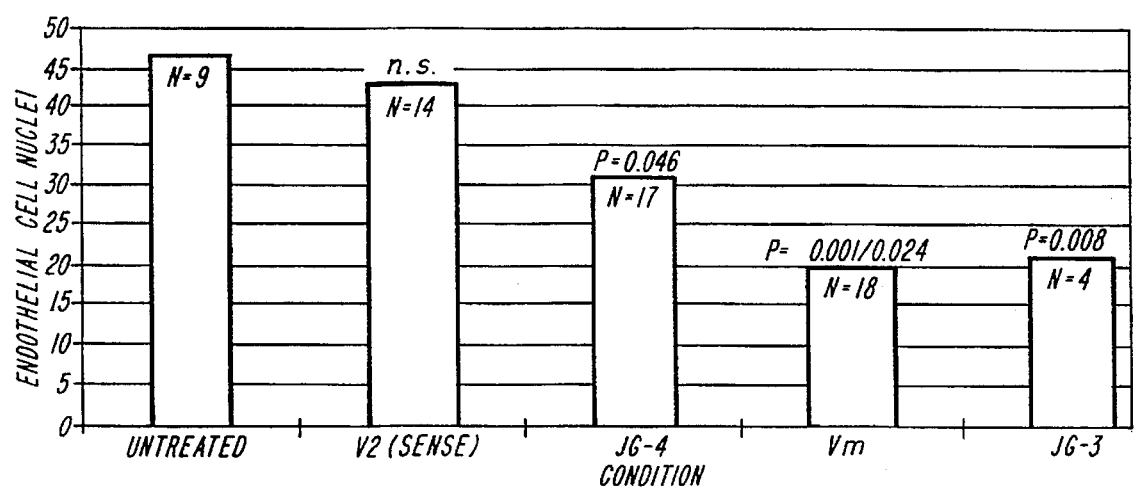
FIG. 2 is a graphic representation of the ability of oligonucleotides of the invention to inhibit neovascularization during retinopathy of prematurity.

A compilation of the results of these experiments is presented in FIG. 2. These results indicate that Vm (SEQ ID NO:46) antisense oligonucleotide significantly reduces retinal neovascularization when compared with both untreated and sense oligonucleotide V2, (SEQ ID NO:49) controls. JG-3 (SEQ ID NO:47) and JG-4 (SEQ ID NO:47) show significant activity when compared against untreated eyes. The sense control oligonucleotide V2 (SEQ ID NO:49) does not show any significant activity when compared with untreated eyes.

In the studies described above, the human VEGF antisense oligonucleotide which corresponds to murine JG-3 is H-1 (SEQ ID NO:1), which is targeted to the 5' untranslated region; that which corresponds to murine JG-4 is H-17 (SEQ ID NO:30), which is targeted to the sequence 5' to and containing the ATG of the translational start site of the human VEGF molecule; and that which corresponds to the murine Vm gene is VH (SEQ ID NO:46), which is targeted to sequences surrounding the translational stop site (TGA) of the human VEGF molecule. These antisense oligonucleotides of the invention are expected to inhibit VEGF expression in human cells in much the same way as the murine antisense oligonucleotides inhibit expression of VEGF in mouse cells.

Human VEGF antisense sequences corresponding to other murine sequences are also known. For example, human oligonucleotide H-6 (SEQ ID NO:12) corresponds to a region spanning murine sequences JG-6 (SEQ ID NO:52) and JG-7 (SEQ ID NO:53), and human oligonucleotide H-2 (SEQ ID NO:5) is in the same region as murine sequence JG-5 (SEQ ID NO:51). It is likely that these sequences have a similar effect on inhibition of VEGF expression and hence on controlling neovascularization.

Figure 4:
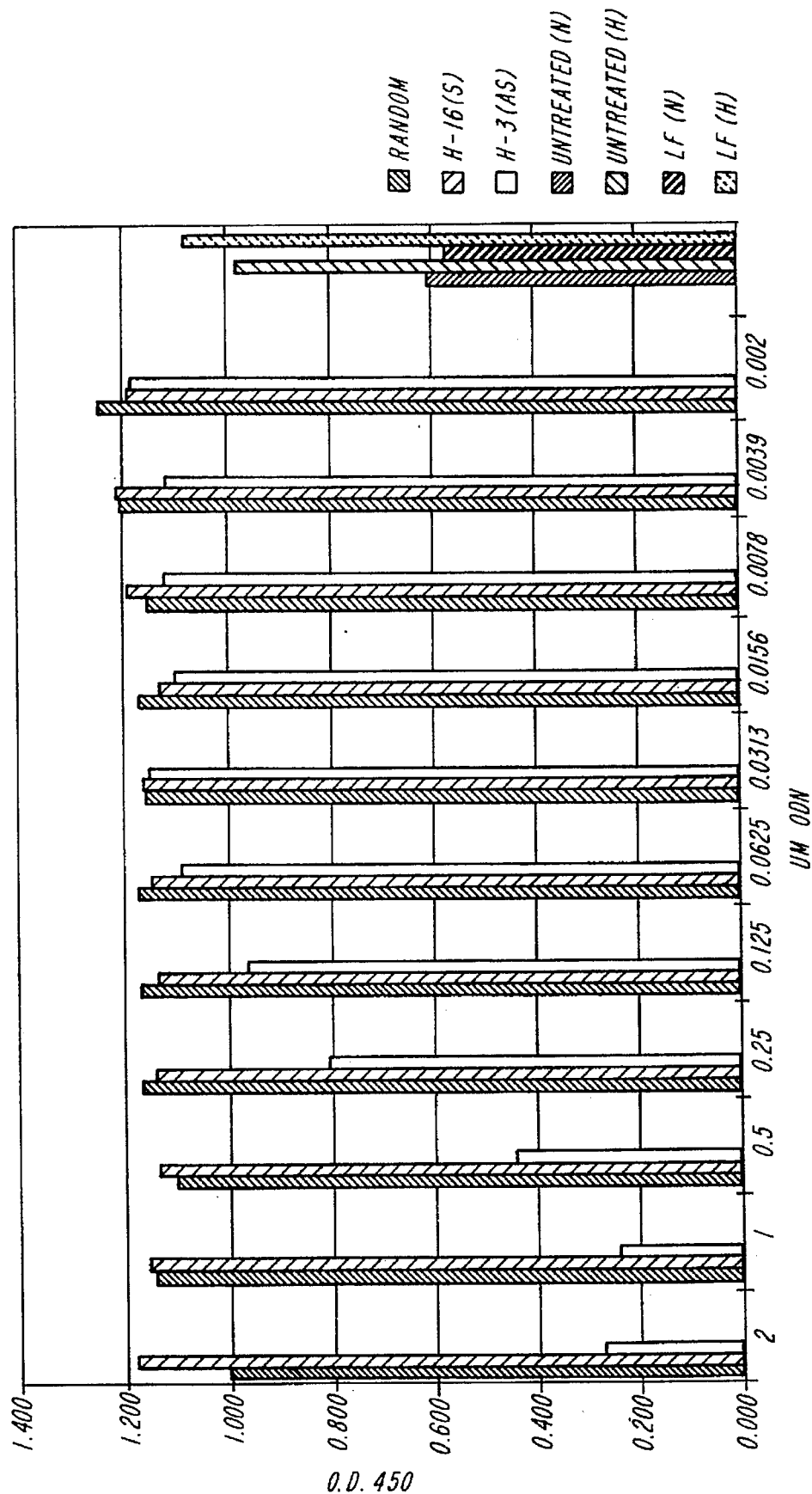
FIG. 4 is a graphic representation of the results of an ELISA demonstrating the reduction in the expression of VEGF in human cells in the presence of human VEGF-specific oligonucleotides of the invention.

There are several methods by which the effects of antisense oligonucleotides on VEGF expression and neovascularization can be monitored. One way is a capture ELISA developed for quantifying human VEGF protein expressed by cells. Using this assay, it has been determined that an antisense phosphorothioate oligonucleotide H-3 (SEQ ID NO:6) targeted to a sequence just 3' to the translational start site can inhibit the hypoxic induction of VEGF expression in a sequence-specific manner, compared with random (R) and sense (H-16, SEQ ID NO:29) controls, as shown in FIG. 4. This inhibition is reproducible and in this in vitro system appears to be lipid carrier-specific and antisense-specific as only antisense oligonucleotide H-3 (SEQ ID NO:6) in the presence of lipofectin (a lipid carrier), and not lipofectamine (another lipid carrier), results in inhibition of VEGF protein expression.

Figure 5:
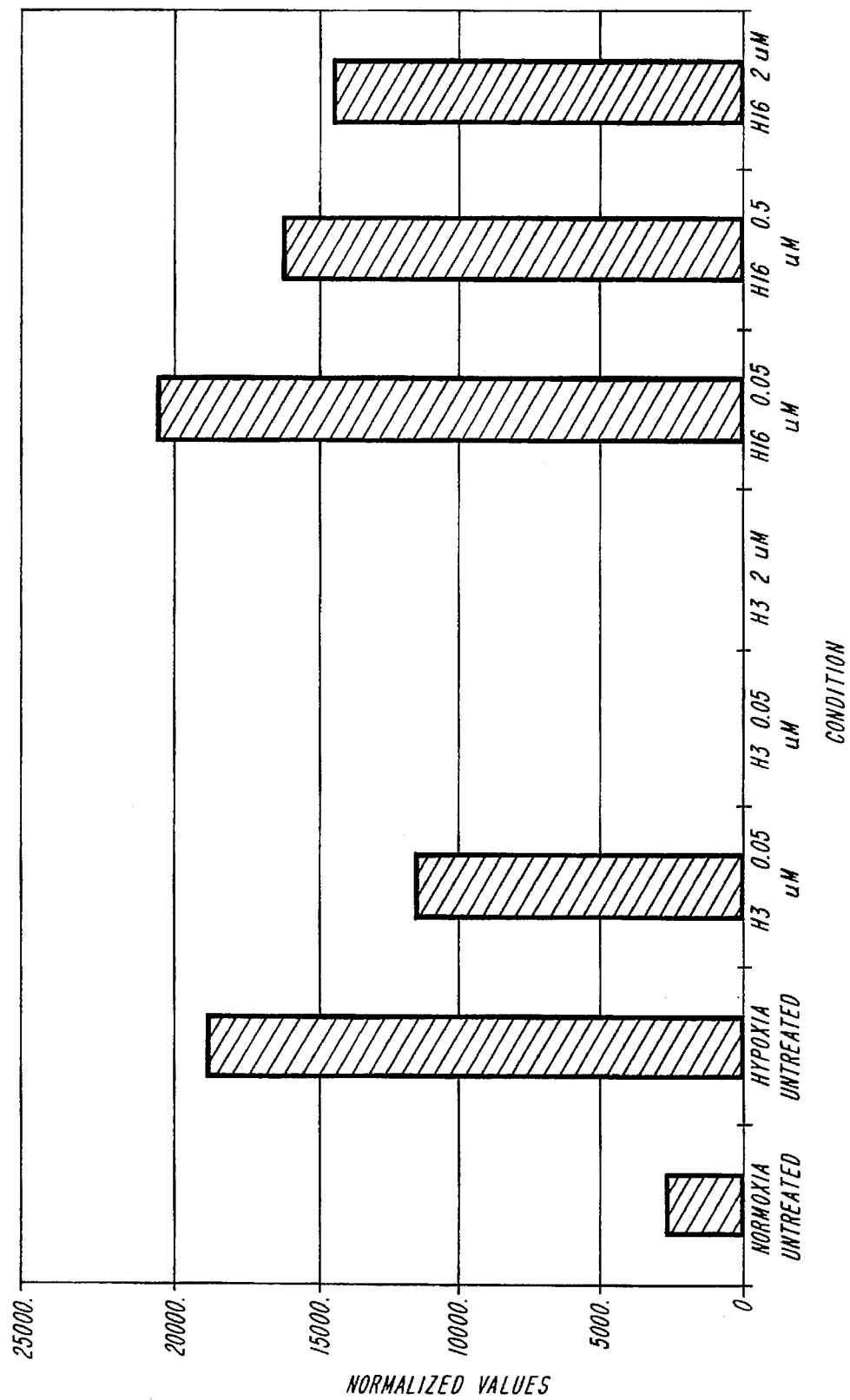
FIG. 5 is a graphic representation of the results of a Northern blot demonstrating the reduction in the expression of VEGF by human cells in the presence of varying concentrations of human VEGF-specific oligonucleotides of the invention.

At the RNA level, Northern blots (Sambrook et al. (1989) *Molecular Cloning; a Laboratory Manual*, Cold Spring Harbor Laboratory Press, New York., Vol. 1, pp. 7.38; Arcellana-Panlilio et al. (1993) *Meth. Enz.* 225:303–328) can be performed to determine the extent that oligonucleotides of the invention inhibit the expression of VEGF mRNA. For example, as shown in FIG. 5, a histogram representing Northern blot analysis demonstrates a decrease in VEGF RNA levels in culture human cells treated with antisense oligonucleotide H-3 (SEQ ID NO:6), while there is only a minimal change in VEGF RNA levels in samples treated with sense control H-16 (SEQ ID NO:29).

In addition, bioactivity can be determined by several methods, including the Miles vessel permeability assay (Miles and Miles (1952) *J. Physiol. (Lond)* 118:228), which measures vessel permeability, endothelial cell mitogenicity, which measures cell growth, and intracellular calcium release in endothelial cells (see, e.g., Brock and Capasso (1988) *J. Cell. Physiol.* 136:54), which measures the release of calcium in response to VEGF binding to its receptor on endothelial cells.

The following examples illustrate the preferred modes of making and practicing the present invention, but are not meant to limit the scope of the invention since alternative methods may be utilized to obtain similar results.

EXAMPLE 1

PREPARATION OF VEGF-SPECIFIC OLIGONUCLEOTIDES

Human VEGF cDNA is transcribed in vitro using an in vitro eukaryotic transcription kit (Stratagene, La Jolla, Calif.). The RNA is labelled with $^{32}P$ using T-4 polynucleotide kinase as described by (Sambrook et al. (1989) *Molcular Cloning: a Laboratory Manual*, Cold Spring Harbor Laboratory Press, New York, Vol. 1, pp. 5.71). The labelled RNA is incubated in the presence of a randomer 20 mer library and RNAse H, an enzyme which cleaves RNA-DNA duplexes (Boehringer Mannheim, Indianapolis, Ind.). Cleavage patterns are analyzed on a 6% polyacrylamide urea gel. The specific location of the cleaved fragments is determined using a human VEGF sequence ladder (Sequenase Kit, United States Biochemical, Cleveland, Ohio).

EXAMPLE 2

ANIMAL MODEL OF RETINAL NEOVASCULARIZATION

A. Preparation of Oligonucleotides

Synthesis of the following oligonucleotides: JG-3 (SEQ ID NO:47), JG-4 (SEQ ID NO:48), Vm (SEQ ID NO:46), and V2 (SEQ ID NO:49), was performed on a Pharmacia Gene Assembler series synthesizer using the phosphoramidite procedure (see, e.g., Uhlmann et al. (Chem. Rev. (1990) 90:534–583). Following assembly and deprotection, oligonucleotides were ethanol precipitated twice, dried, and suspended in phosphate-buffered saline (PBS) at the desired concentration.

The purity of these oligonucleotides was tested by capillary gel electrophoreses and ion exchange HPLC. Endotoxin levels in the oligonucleotide preparation was determined using the Luminous Amebocyte Assay (Bang (1953) *Biol. Bull.* (Woods Hole, Mass.) 105:361–362).

B. Preparation of Animal Model

Seven day postnatal mice (P7, C57b1/6J, (Children's Hospital Breeding Facilities, Boston, Mass.) were exposed to 5 days of hyperoxic conditions (75±2%) oxygen in a sealed incubator connected to a Bird 3-M oxygen blender (flow rate: 1.5 liters/minute; Bird, Palm Springs, Calif.). The oxygen concentration was monitored by means of an oxygen analyzer (Beckman, Model D2, Irvine, Calif.). After 5 days (P12), the mice were returned to room air. Maximal retinal neovascularization was observed 5 days after return to room air (P17). After P21, the level of retinal neovascularization was just beginning to regress.

C. Treatment

After mice had been removed from oxygen, antisense oligonucleotides were injected into the vitreous with a Hamilton syringe and a 33 gauge needle (Hamilton Company, Reno, Nev.). The animals were anesthetized for the procedure with Avertin ip. The mice were given a single injection of antisense oligonucleotides (or sense or nonsense controls) at P12 achieving a final concentration of approximately 30 µM. The animals were sacrificed at P17 with tribromoethanol ip (0.1 ml/g body weight) and cervical dislocation.

D. Microscopy

The eyes were enucleated, fixed in 4% paraformaldehyde, and embedded in paraffin. Serial sections of the whole eyes were cut sagittally, through the cornea, and parallel to the optic nerve. The sections were stained with hematoxylin and periodic acid-Schiff (PAS) stain. The extent of neovascularization in the treated eyes was determined by counting endothelial cell nuclei extending past the internal limiting membrane into the vitreous. Nuclei from new vessels and vessel profiles could be distinguished from other structures in the retina and counted in cross-section with light microscopy. Additional eyes were sectioned and examined by in situ hybridization to a VEGF probe.

To examine the retinal vasculature using fluorescein-dextran, the mice were perfused with a 50 mg/ml solution of high molecular weight fluorescein-dextran (Sigma Chemical Company, St. Louis, Mo.) in 4% paraformaldehyde. The eyes were enucleated, fixed in paraformaldehyde, and flat-mounted with glycerol-gelatin. The flat-mounted retinas were viewed and photographed by fluorescence microscopy using an Olympus BX60 fluorescence microscope (Olympus America Corp., Bellingham, Mass.).

EXAMPLE 3

RETINOPATHY OF PREMATURITY

A. Preparation of Oligonucleotides

VEGF specific oligonucleotides are synthesized as described in EXAMPLE 2A above. Sterile and endotoxin-free oligonucleotides are diluted in Balanced Salt Solution (BSS, Alcon, Fort Worth, Tex.) so as to have the same pH and electrolyte concentration as the aqueous or vitreous of the eye. Emalphor EC620 (2.5%, GAF Corp.) (Bursell et al. (1993) *J. Clin. Invest.* 92:2872–2876), a petroleum product, is added to change viscosity and aid in delivery properties. Doses to achieve intravitreal concentrations ranging from 0.1 µM–100 µM are administered depending on the severity of the retinal/ocular neovascularization. The volume delivered is between 1 µl and 1 ml depending on the volume of the eye.

B. ROP Patient Profile

The patient treated is a premature, 34 week post-conception Caucasian female weighing less than 1,000 grams at birth and is respirator-dependent. The patient has bilateral stage 3+ disease with 11 clock hours of neovascularization in each eye. There is hemorrhaging in one eye, and both eyes have reached "threshold"0 according to the international classification (i.e., each eye has >50% chance of going on to retinal detachment). Extraretinal fibrovascular proliferation is found in both eyes.

C. Treatment

The intubated patient is anesthetized with fluorane. The face and eyes are prepared with a betadine scrub and draped in the usual sterile fashion. The sterile drug with vehicle is injected with a 33 gauge needle on a sterile syringe at the posterior limbus (pars plana) through full thickness sclera into the vitreous. No closing suture is required unless there is leakage. Antibiotic drops containing gentamicin or erythromycin ointment is applied to the surface of the globe in the palpebral fissure several times per day until there is complete wound closure. The frequency of injection ranges from every other day to once every 6 months or less, depending on the severity of the disease process, the degree of intraocular inflammation, the character of the vehicle (i.e., slow release characteristics), the degree of inhibition of the neovascularization and the tolerance of the eye to injections. Short and long term follow-up check-ups for possible retinal detachment from the neovascular disease as well as from the injections are necessary.

D. Monitoring of Progress

The eye upon dilation is monitored for signs of inflammation, infection, and resolution of neovascularization by both a direct and a indirect ophthalmoscope to view the retina and fundus. A slit lamp exam is used in some cases of anterior segment disease. Positive response to treatment includes fewer neovascular tufts, fewer clock hours of involvement, and less tortuosity of large blood vessels. Monitoring can be as frequent as every day in cases where premature infants are threatened with retinal detachment from proliferative ROP. The frequency of monitoring will diminish with resolution of neovascularization.

EXAMPLE 4

DIABETIC RETINOPATHY

A. Preparation of Oligonucleotides

VEGF specific oligonucleotides are synthesized as described in EXAMPLE 2A above and prepared for administration as described in EXAMPLE 3A above. Doses to achieve intravitreal concentrations ranging from 0.1–100 µM are administered depending on the severity of the retinal/ocular neovascularization. The volume delivered is between 1 µl and 1 ml depending on the volume of the eye and whether vitreous has been previously removed as during a vitrectomy for diabetic eye disease.

B. Diabetic Patient Profile

The patient to be treated is a 30 year old African American male suffering for 25 years from juvenile-onset diabetes. The patient has bilateral proliferative retinopathy with sub-retinal hemorrhaging, cotton wool spots, and exudates. Upon fluorescein angiography, there are well defined areas of neovascularization bilaterally with areas of capillary drop-out.

C. Treatment

The patient is treated weekly with intraocular injections of oligonucleotides resuspended in the appropriate vehicle (BSS, Emanfour) at concentrations within the range of 0.1–100 µM. The treatment may be supplemented with systemic delivery of oligonucleotide (i.e., intravenous, subcutaneous, or intramuscular) from 2 to 5 times per day to once a month, depending on the disease process and the biological half life of the oligonucleotides.

D. Monitoring of Progress

The patient's eyes are monitored as described above in EXAMPLE 2D. The eyes upon dilation are examined for regression of neovascularization with both a direct and an indirect ophthalmoscope to view the retina and fundus. A slit lamp exam is used in the case of anterior segment disease. Repeat injections are given as needed, based on the degree of inhibition of the neovascularization and the tolerance of the eye to injections. Short and long term follow-up check-ups are given to check for possible retinal detachment from the neovascular disease as well as from the injections.

EXAMPLE 5

AGE-RELATED MACULAR DEGENERATION

A. Preparation of Oligonucleotides

VEGF specific oligonucleotides are synthesized as described in EXAMPLE 2A above and prepared as described in EXAMPLE 3A above. Doses to achieve intravitreal concentrations ranging from 1 µl and 1 ml are administered depending on the severity of the retinal/ocular neovascularization. The volume delivered is between 1 µl and 1 ml depending on the volume of the eye and whether vitreous has been previously removed.

B. ARMD Patient Profile

The patient is a 50 year old Caucasian male suffering from the exudative form of age related macular degeneration. This patient has choroidal neovascularization which is apparent from fluorescein angiography. The disease is bilateral and the patient has a reduction in vision in each eye from 20/60 to 20/100.

C. Treatment

The patient is treated weekly with intraocular injections of oligonucleotide resuspended in the appropriate vehicle (BSS, Emanfour) at concentrations within the range of 0.1 to 100 µM. This treatment may be supplemented with systemic delivery of oligonucleotide (i.e., intravenous, subcutaneous, or intramuscular) from 2 to 5 times per day to once a month.

D. Monitoring of Progress

The eyes upon dilation are examined for regression of neovascularization with both a direct and an indirect ophthalmoscope to view the retina and fundus. Fluorescein angiography is used to check for the resolution of neovascularization. A slit lamp exam is used in the case of anterior segment disease. Repeat injections are given as needed, based on the degree of inhibition of the neovascularization and the tolerance of the eye to injections. Short and long term follow-up check-ups are given to check for possible retinal detachment from the neovascular disease as well as from the injections.

EXAMPLE 6

HUMAN CELL CULTURE

U373 human neuroblastoma cells were cultured in Dulbecco's modified Earls (DME) medium containing glucose (4500 mg/ml) and glutamate (2 mM) (Mediatech, Washington, D.C.) supplemented with penicillin/streptomycin (100 IU/MI/100 mcg/ml, Mediatech, Washington, D.C.). The cells were cultured at 37° C. under 10% $CO_2$. The cells were plated in 96 well tissue culture dishes (Costar Corp., Cambridge, Mass.) and maintained as above. The cells were placed under anoxic conditions for 18–20 hours using an anaerobic chamber (BBL Gas Pak, Cockeysville, Md.).

EXAMPLE 7

NORTHERN BLOTTING

In order to determine the level at which inhibition of VEGF expression occurs in cells in the presence of an oligonucleotide of the invention, Northern blotting was carried out. Human U373 cells cultured as described in EXAMPLE 6 above were plated in 100 mm tissue culture dishes and treated for 12 hours in the presence of 5 µg/ml lipofectin (Gibco-BRL, Gaithersburg, Md.) as a lipid carrier with oligonucleotide H-3 (SEQ ID NO:6) (antisense oligonucleotide) and H-16 (SEQ ID NO:29) (sense oligonucleotide) at 0.05 µM, 0.5 µM, and 2.0 µM, respectively. The cells were refed after 12 to 15 hours with fresh media+oligonucleotide (minus lipofectin) and allowed to recover for 5 to 7 hours. The cells were placed in hypoxia for 18 to 20 hours total RNA was isolated using the single-step acid guanidinium thiocyanate-phenol-chloroform extraction method described by Chomczynski and Sacchi (*Anal. Biochem.* (1987) 162:156–159). Northern blotting was performed according to the methods of Sambrook et al. (*Molecular Cloning: Laboratory Manual*, Cold Spring Harbor Laboratory Press, New York) (1989) Vol. 1, pp. 7.38) or Arcellana-Panlilio et al. (*Meth. Enz.* (1993) 225:303–328). All RNA signals were quantified on a Phosphorimager (BioRad, Hercules, Calif.) and normalized using the 36B4 cDNA probe (Laborda (1991) *Nucleic Acids Res.* 19:3998).

EXAMPLE 8

ELISA VEGF PROTEIN STUDY

U373 neuroblastoma cells as described in EXAMPLE 6 above were plated in a 96 well tissue culture dish and treated overnight with varying concentrations of antisense oligonucleotides against human VEGF in the presence of 5 μg/ml lipofectin. The cells were refed after 12 to 15 hours with fresh media+oligonucleotide (no lipofectin) and allowed to recover for 5 to 7 hours. The dishes were placed under hypoxic conditions for 18 to 20 hours using an anaerobic chamber (Gas Pac, Cockeysville, Md.). The media was analyzed using the antigen capture ELISA assay described above (approximately 36 hours post treatment). The human VEGF oligonucleotides used were H-3 (SEQ ID NO:6) (antisense, coding), H-16 (SEQ ID NO:29) (start site/coding, sense control), and a random control (R).

Figure 3:
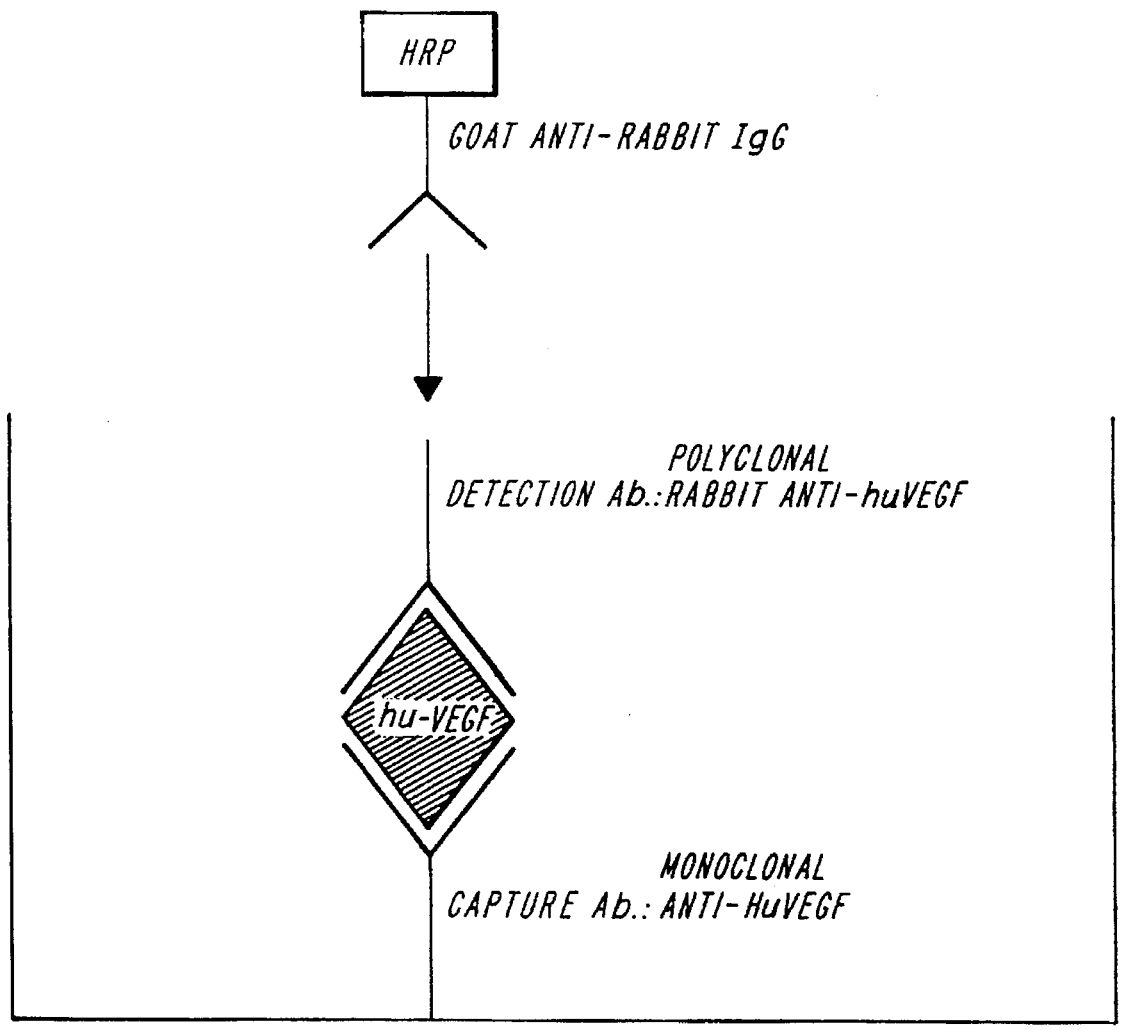
FIG. 3 is a diagrammatic representation of the ELISA used to test the ability of human VEGF-specific oligonucleotides to inhibit the expression of VEGF.

The culture medium from the cells described in EXAMPLE 5 was analyzed for VEGF protein as follows. 96-well plates (Maxizorb ELISA Nunc A/S, Camstrup, Denmark) were treated overnight at 4° C. with 100 μl/well of the capture antibody, a monoclonal antibody against human VEGF (R&D Systems, Minneapolis, Minn., 2.5 μg/ml in 1× PBS). The wells were washed three times with 1× PBS/0.05% Tween-20 (United States Biochemical, Cleveland, Ohio) using a plate washer (Dynatech, Gurnsey Channel Islands). Non-specific binding sites in the wells were blocked by adding 2% normal human serum (100 μl) and incubating the plate at 37° C. for 2 hours. This blocking solution was removed and 200 μl conditioned medium containing human VEGF added to each well and incubated at 37° C. for 2 to 3 hours. The plates were washed as described above. 100 μl of the primary antibody (618/619, 2 μg/ml in normal human serum) was added to each well and incubated at 37° C. for 1 to 2 hours. The secondary antibody was an affinity purified rabbit anti-human VEGF polyclonal). The plates were washed as described above. 100 μl of the detection antibody, a horse radish peroxidase-labelled goat anti-mouse IgG monoclonal antibody (1:10, 000, Vector Laboratories, Burlinggame, Calif.), was added to each well and incubated at 37° C. for 1 hour. The plates were washed as described above. The wells were developed using the TMB microwell peroxidase developing system (Kirkegaard and Perry, Gaithersburg, Md.), and quantified at 450 nm using a Ceres 900 plate reader (Bio-Tek instruments, Inc., Winooski, Vt.). The linear range of this assay is between 2 ng and 0.01 ng human VEGF. Representative results are shown in FIG. 3.

EXAMPLE 9

BIOACTIVITY ASSAYS

Bioactivity can be determined by the Miles vessel permeability assay (Miles and Miles (1952) *J. Physiol. (Lond.)* 118:228). Briefly, Hartley guinea pigs (800 g) are shaved and depilated and injected intravenously with 1.0 ml of normal saline containing 0.5 g of Evans Blue dye per 100 ml. Subcutaneous injections (250 μl) of serum-free medium containing unknown quantities of VEGF are performed. Positive (purified VEGF) and negative controls (normal saline) are also included in the experiment. Twenty minutes post-injection, the animals are sacrificed and the test and control sites are cut out and quantitated for extravasation of Evans Blue dye. The limit of detection for this assay is 500 pM.

Endothelial cell mitogenicity can also manifest bioactivity. In this method, human umbilical vein endothelial (HUVEC) are grown and maintained using the Biocoat endothelial cell growth environment (Collaborative Biomedical Products, Bedford, Mass.). $1 \times 10^4$ cells are then plated in duplicate on 35 mM tissue culture dishes in 1.4 ml E-STIM medium (Collaborative Biomedical Products, Bedford, Mass.) plus 5% heat-inactivated fetal bovine serum. Following cell attachment (about 4 hours), two dishes of cells are trypsinized, counted, and used for a starting cell number. Test samples containing unknown amounts of VEGF are then added in duplicate to the remaining dishes at day 0 and at day 2. Controls consisting of purified VEGF (positive) and PBS (negative) are also used. On day 4, the dishes of cells are trypsinized, counted and compared to the starting cell number. The limit of detection for this assay is 10 pM.

The intracellular calcium release assay is also used to monitor bioactivity (see, e.g., Brock and Capasso (1988) *J. Cell. Physiol.* 136:54). Human umbilical vein endothelial cells (HUVEC) are maintained in EGM-UV medium. Cells are removed from the plate by means of EDTA and collagenase. The calcium-sensitive dye, Fura-2 (Molecular Probes, Eugene, Oreg.), is used to monitor changes in the concentration of intracellular calcium. In brief, medium containing an unknown concentration of VEGF is added to an aliquot of suspended HUVEC, pre-loaded with Fura-2. Changes in fluorescence representing changes in intracellular calcium release are measured using a Hitachi 2000° F. fluorometer. Positive (histamine, thrombin) and negative (EGTA) controls are also analyzed. This method is extremely sensitive and has a limit of detection of 0.2 pM.

EQUIVALENTS

Those skilled in the art will recognize, or be able to ascertain, using no more than routine experimentation, numerous equivalents to the specific substances and procedures described herein. Such equivalents are considered to be within the scope of this invention, and are covered by the following claims.

---

What is claimed is:

1. A synthetic oligonucleotide complementary to human VEGF mRNA, the oligonucleotide having a nucleotide sequence selected from the group consisting SEQ ID NOs: 1, 2, 6, 14, 15, 18, 28, 30, 31, and 32.

* * * * *

SEQUENCE LISTING ( 1 ) GENERAL INFORMATION:

( i i i ) NUMBER OF SEQUENCES: 53

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:1:

CGCCGGGCCG CCAGCACACT                    20

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: RNA ( i i i ) HYPOTHETICAL: NO ( i v ) ANTI-SENSE: YES ( x i ) SEQUENCE DESCRIPTION: SEQ ID NO:2:

CGCCGGGCCG CCAGCACACU                    20

( 2 ) INFORMATION FOR SEQ ID NO:3:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:3:

GGCCGCCAGC ACACT                    15

( 2 ) INFORMATION FOR SEQ ID NO:4:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:4:

GCTCGCGCCG GGCCGCCAGC ACACT                    25

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:5:

CAAGACAGCA GAAAGTTCAT                                                      20

( 2 ) INFORMATION FOR SEQ ID NO:6:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:6:

CACCCAAGAC AGCAGAAAG                                                       19

( 2 ) INFORMATION FOR SEQ ID NO:7:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:7:

CACCCAAGAC AGCAG                                                           15

( 2 ) INFORMATION FOR SEQ ID NO:8:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:8:

CCAATGCACC CAAGACAGCA GAAAG                                                25

( 2 ) INFORMATION FOR SEQ ID NO:9:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:9:

ACGCACACAG AACAAGACG                                                       19

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:10:

AAGTTCATGG TTTCGGAGGC        20

( 2 ) INFORMATION FOR SEQ ID NO:11:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:11:

GTTCATGGTT TCGGAGGCCC        20

( 2 ) INFORMATION FOR SEQ ID NO:12:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:12:

GTGCAGCCTG GGACCACTTG        20

( 2 ) INFORMATION FOR SEQ ID NO:13:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:13:

CGCCTCGGCT TGTCACATCT        20

( 2 ) INFORMATION FOR SEQ ID NO:14:

(i) SEQUENCE CHARACTERISTICS:
  (A) LENGTH: 20 base pairs
  (B) TYPE: nucleic acid
  (C) STRANDEDNESS: single
  (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:14:

CTTCCTCCTG CCCGGCTCAC    20

(2) INFORMATION FOR SEQ ID NO:15:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: RNA (iii) HYPOTHETICAL: NO (iv) ANTI-SENSE: YES (xi) SEQUENCE DESCRIPTION: SEQ ID NO:15:

CUUCCUCCUG CCCGGCUCAC    20

(2) INFORMATION FOR SEQ ID NO:16:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:16:

CTTCCTCCTG CCCGG    15

(2) INFORMATION FOR SEQ ID NO:17:

(i) SEQUENCE CHARACTERISTICS:
    (A) LENGTH: 25 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:17:

GGCTCCTTCC TCCTGCCCGG CTCAC    25

(2) INFORMATION FOR SEQ ID NO:18:

(i) SEQUENCE CHARACTERISTICS:
    (A) LENGTH: 20 base pairs
    (B) TYPE: nucleic acid
    (C) STRANDEDNESS: single ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:18:

GTCTCCTCTT CCTTCATTTC 20

( 2 ) INFORMATION FOR SEQ ID NO:19:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:19:

GTCTCCTCTT CCTTC 15

( 2 ) INFORMATION FOR SEQ ID NO:20:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:20:

GCAGAGTCTC CTCTTCCTTC ATTTC 25

( 2 ) INFORMATION FOR SEQ ID NO:21:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:21:

CGGACCCAAA GTGCTCTGCG 20

( 2 ) INFORMATION FOR SEQ ID NO:22:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:22:

CCAAAGTGCT CTGCG 15

( 2 ) INFORMATION FOR SEQ ID NO:23:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:23:

CCCTCCGGAC CCAAAGTGCT CTGCG 25

( 2 ) INFORMATION FOR SEQ ID NO:24:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:24:

GGGCACGACC GCTTACCTTG 20

( 2 ) INFORMATION FOR SEQ ID NO:25:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:25:

GGGACCACTG AGGACAGAAA 20

( 2 ) INFORMATION FOR SEQ ID NO:26:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:26:

CACCACTGCA TGAGAGGCGA 20

( 2 ) INFORMATION FOR SEQ ID NO:27:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:27:

TCCCAAAGAT GCCCACCTGC 20

( 2 ) INFORMATION FOR SEQ ID NO:28:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:28:

CGCATAATCT GGAAAGGAAG 20

( 2 ) INFORMATION FOR SEQ ID NO:29:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:29:

ACTTTCTGCT GTCTTGGGTG 20

( 2 ) INFORMATION FOR SEQ ID NO:30:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:30:

CATGGTTTCG GAGGCCCGAC 20

( 2 ) INFORMATION FOR SEQ ID NO:31:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: cDNA/RNA ( i i i ) HYPOTHETICAL: NO ( i v ) ANTI-SENSE: YES ( x i ) SEQUENCE DESCRIPTION: SEQ ID NO:31:

CAUGGTUUCG GAGGCCCGAC 20

( 2 ) INFORMATION FOR SEQ ID NO:32:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:32:

TTCATGGTTT CGGAGGCCCG 20

( 2 ) INFORMATION FOR SEQ ID NO:33:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:33:

GACCGCTTAC CTTGGCATGG 20

( 2 ) INFORMATION FOR SEQ ID NO:34:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:34:

CCTGGGACCA CTGAGGACAG 20

( 2 ) INFORMATION FOR SEQ ID NO:35:

( i ) SEQUENCE CHARACTERISTICS:

( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:35:

GGGACTCACC TTCGTGATGA 20

( 2 ) INFORMATION FOR SEQ ID NO:36:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:36:

GAACTTCACC ACTGCATGAG 20

( 2 ) INFORMATION FOR SEQ ID NO:37:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:37:

TCCCAAAGAT GCCCACCTGC 20

( 2 ) INFORMATION FOR SEQ ID NO:38:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:38:

GCATAATCTG GAAAGGAAGG 20

( 2 ) INFORMATION FOR SEQ ID NO:39:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear 5,639,872

37

38

-continued (i i) MOLECULE TYPE: cDNA (i i i) HYPOTHETICAL: NO (i v) ANTI-SENSE: YES (x i) SEQUENCE DESCRIPTION: SEQ ID NO:39:

ACATCCTCAC CTGCATTCAC                                                        20

(2) INFORMATION FOR SEQ ID NO:40:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (i i) MOLECULE TYPE: cDNA (i i i) HYPOTHETICAL: NO (i v) ANTI-SENSE: YES (x i) SEQUENCE DESCRIPTION: SEQ ID NO:40:

ACATCCUCAC CTGCAUUCAC                                                        20

(2) INFORMATION FOR SEQ ID NO:41:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (i i) MOLECULE TYPE: cDNA (i i i) HYPOTHETICAL: NO (i v) ANTI-SENSE: YES (x i) SEQUENCE DESCRIPTION: SEQ ID NO:41:

TTTCTTTGGT CTGCAATGGG                                                        20

(2) INFORMATION FOR SEQ ID NO:42:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (i i) MOLECULE TYPE: cDNA (i i i) HYPOTHETICAL: NO (i v) ANTI-SENSE: YES (x i) SEQUENCE DESCRIPTION: SEQ ID NO:42:

GGCCACTTAC TTTCTTGTC                                                         20

(2) INFORMATION FOR SEQ ID NO:43:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (i i) MOLECULE TYPE: cDNA (i i i) HYPOTHETICAL: NO ( i v ) ANTI-SENSE: YES ( x i ) SEQUENCE DESCRIPTION: SEQ ID NO:43:

CACAGGGACT GGAAAATAAA 20

( 2 ) INFORMATION FOR SEQ ID NO:44:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:44:

GGGAACCAAC CTGCAAGTAC 20

( 2 ) INFORMATION FOR SEQ ID NO:45:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:45:

GTCACATCTG AGGGAAATGG 20

( 2 ) INFORMATION FOR SEQ ID NO:46:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:46:

CAGCCTGGCT CACCGCCTTG G 21

( 2 ) INFORMATION FOR SEQ ID NO:47:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:47:

```
TCGCGCTCCC TCTCTCCGGC                                                     20
```

( 2 ) INFORMATION FOR SEQ ID NO:48:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:48:

```
CATGGTTTCG GAGGGCGTC                                                      19
```

( 2 ) INFORMATION FOR SEQ ID NO:49:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:49:

```
TCCGAAACCA TGAACTTTCT G                                                   21
```

( 2 ) INFORMATION FOR SEQ ID NO:50:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:50:

```
GGTTTCGGAG GCCCGACCG                                                      19
```

( 2 ) INFORMATION FOR SEQ ID NO:51:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:51:

```
CAAGAGAGCA GAAAGTTCAT                                                     20
```

( 2 ) INFORMATION FOR SEQ ID NO:52:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:52:

CACCCAAGAG AGCAGAAACT        20

( 2 ) INFORMATION FOR SEQ ID NO:53:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:53:

TCGTGGGTGC AGCCTGGGAC        20